Figure 1:
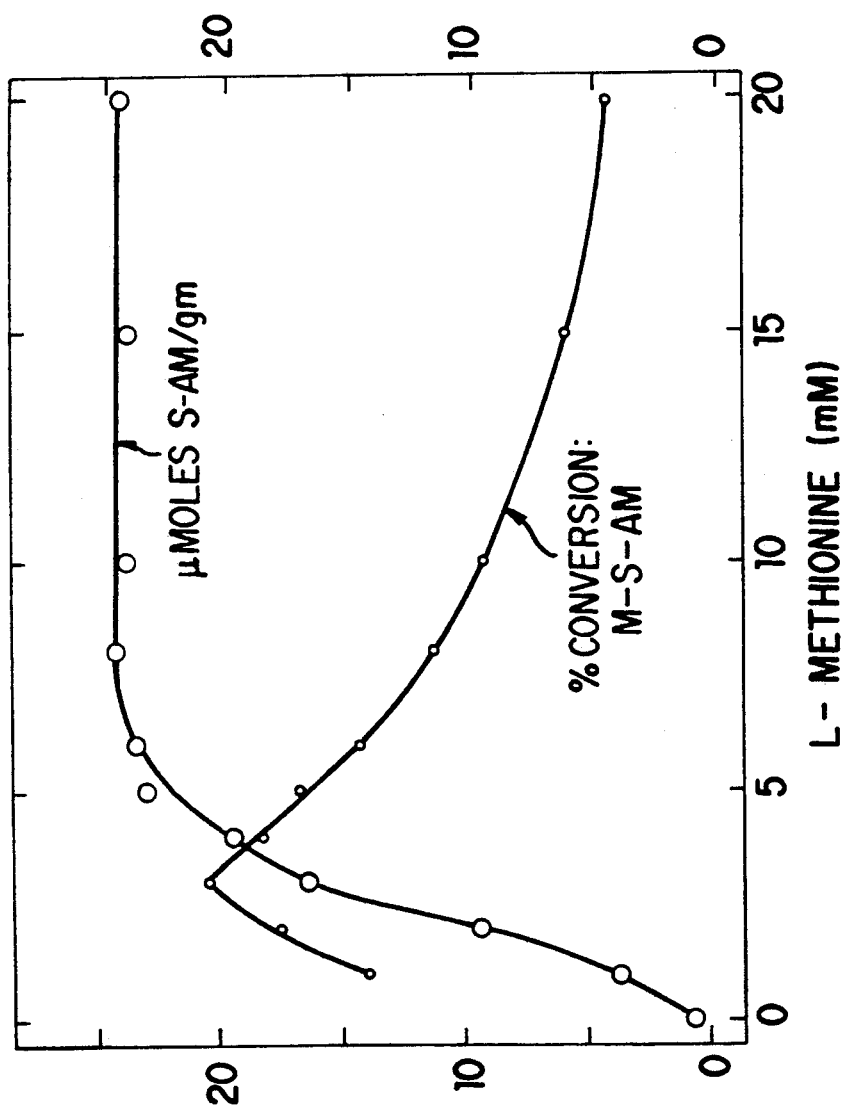

United States Patent [19]

Gennari

[11] Patent Number: 5,128,249

[45] Date of Patent: * Jul. 7, 1992

[54] STABLE SULPHO-ADENOSYL-L-METHIONINE (SAME) SALTS, PARTICULARLY SUITABLE FOR ORAL PHARMACEUTICAL USE

[75] Inventor: Federico Gennari, Truccazzano, Italy

[73] Assignee: Bioresearch S.p.a., Milan, Italy

[*] Notice: The portion of the term of this patent subsequent to Nov. 4, 2003 has been disclaimed.

[21] Appl. No.: 731,722

[22] Filed: May 8, 1985

[30] Foreign Application Priority Data

May 16, 1984 [IT] Italy .................. 20940 A/84

[51] Int. Cl.$^5$ ............... C12P 13/12; C12N 1/18; C07H 19/06
[52] U.S. Cl. ..................... 435/113; 435/256; 536/26
[58] Field of Search ............ 435/88, 113, 84, 85, 435/87, 255, 256; 536/26

[56] References Cited

U.S. PATENT DOCUMENTS

| | | | |
|---|---|---|---|
| 3,893,999 | 7/1975 | Fiecchi | 536/26 |
| 3,954,726 | 5/1976 | Fiecchi | 435/119 |
| 4,057,686 | 11/1977 | Fiecchi | 536/26 |
| 4,562,149 | 12/1985 | Shiozaki et al. | 435/88 |
| 4,621,056 | 11/1986 | Gennari | 435/85 |

FOREIGN PATENT DOCUMENTS 0107485 9/1978 Japan ................... 536/26

2064523 6/1981 United Kingdom.

Primary Examiner—Elizabeth C. Weimar
Attorney, Agent, or Firm—Stevens, Davis, Miller & Mosher

[57] ABSTRACT

This invention relates to new stable sulpho-adenosyl-L-methionine (SAMe) salts and the relative production process.

Said salts have the following general formula:

$$SAMe \cdot nR(O)_m(SO_3H)_p \qquad (I)$$

where m can be zero or 1; n is 1.5 when p is 2, and is 3 when p is 1; R is chosen from the group consisting of alkyl, phenylalkyl and carboxyalkyl, in which the linear or branched alkyl chain contains from 8 to 18 carbon atoms.

In particular, the salts according to the present invention are SAMe salts of sulphonic acids, or of sulphuric acid esters, or of dioctylsulphosuccinic acid, which fall within formula (I).

The process for producing said salts consists of: a) enriching the starting yeast with SAMe; b) lysing the cells and recovering an aqueous solution rich in SAMe (cell lysate); c) purifying the lysate by ultrafiltration; d) precipitating the SAMe by treatment with one of the aforesaid acids or esters; e) separating the precipitated product, washing it and drying it under vacuum.

6 Claims, 1 Drawing Sheet

STABLE SULPHO-ADENOSYL-L-METHIONINE (SAME) SALTS, PARTICULARLY SUITABLE FOR ORAL PHARMACEUTICAL USE

This invention relates to new stable sulpho-adenosyl-L-methionine (SAMe) salts.

More particularly, the invention relates to SAMe salts of sulphonic acids or of long-chain sulphuric esters or of dioctylsulphosuccinate, particularly suitable for oral pharmaceutical use, and the relative production process.

Sulpho-adenosyl-L-methionine (SAMe) is the main biological donor of methyl groups, becasue of which it has recently found important therapeutic applications.

The main problems connected with the large-scale use of this product are its thermal instability even at ambient temperature, and its preparation and purification complexity.

Said product has therefore been the subject of numerous patents directed both towards the production of new stable salts and towards the provision of preparation processes which can be implemented on an industrial scale.

The present applicant has filed certain patents relating both to new stable salts and to preparation methods for sulpho-adenosyl-L-methionine (Italian patents 1,043,885, 1,002,016, 1,002,036 and 1,054,175; Italian patent applications 23603A/81 and 22622A/83).

Currently known SAMe salts are all highly soluble in water, hydroscopic, strongly acid and particularly suitable for injectable pharmaceutical formulations. However, the widespread use of these salts in pharmaceutical formulations for oral administration involves serioud problmes connected with the particular hygroscopic nature of SAMe sals which make it difficult to manipulate the powders which contain them, and with the pore SAMe absorption into the gastro-intestinal tract, which does not enable suitable hematic levels to be reached for obtaining the required pharmacological action.

The situation in this sense of substantially improved by using gastroresistant formulations as already patented by the present applicant (Italian patent application 22621A/83).

The situation is however still far from perfect in that experimental data on animals indicate a bioavilability on oral administration which ranges from 3% to 20% according to the experimental model used.

We have now discovered new SAMe salts which are stable at ambient temperature, insoluble in water and soluble in many organic solvents such as alcohols, 1:1 methanol-chloroform mixture, 1:1 ethanol-chloroform mixture, acetone and other medium polarity solvents, which allow high absorption into the gastro-intestinal tract, to reach a bioavailability on oral administration of the order of as much as 70–80%.

These therefore represent the ideal solution for oral pharmaceutical formulations containing S-adenosyl-L-methionine, because of their non-hygroscopic nature and their absorption into the gastro-intestinal tract.

We have also found that said SAMe salts can be obtained by a new process which has considerable advantages of simplicity and economy over known processes.

The SAMe salts according to the present invention are characterised by the following general formula:

$$SAMe.nR(O)_m(SO_3H)_p \qquad (I)$$

where m can be zero or 1; n is 1.5 when p is 2, and is 3 when p is 1; R is chosen from the group consisting of alkyl, phenylalkyl and carboxyalkyl, in which the linear or branched alkyl chain contains from 8 to 18 carbon atoms.

In particular, the salts according to the present invention are constituted by SAMe salts of sulphonic acids, or SAMe salts of sulphuric acid esters, or SAMe salts of dioctylsulphosuccinic acid which fall with in the aforesaid formula (I), in which the term "dioctylsulphosuccinic acid" signifies the free acid of the commerical product "dioctylsulphosuccinate".

The process for producing SAMe salts according to the present invention is characterised by: a) enriching the starting yeast with SAMe; b) lysing the cells and recovering a solution rich in SAMe (lysate); c) purifying the lysate by ultrafiltration; d) precipitating the SAMe by treatment with one of the aforesaid acids or esters; e) separating and washing the product, and drying it under vacuum.

These and further characteristics and advantages of the SAMe salts according to the present invention and of the relative production process will be more apparent from the detailed description given hereinafter which relates to preferred methods of implementing the various stages of the process and to the results of tests on the absorption of the SAMe salt in the gastro-intestinal tract, and is given for non-limiting illustrative purposes only.

The process according to the present invention enables SAMe salts corresponding to the aforesaid general formula (I) to be obtained easily and economically. In this respect, as said SAMe salts are insoluble in water, they can be obtained with a good degree of insoluble in water, they can be obtained with a good degree of purity by direct precipitation from cell lysates or equivalent fermentation broths containing the SAMe, by virtue of the treatment with sulphonic acids or sulphuric acid esters or dioctylsulphosuccinate, as heretofore defined, to obtain SAMe salts in accordance with formula (I).

Long-chain sulphonic acids are partly available commercially in the form of their sodium salts, or alternatively can be easily prepared from the corresponding bromides by treatment with sodium sulphite in accordance with the reaction:

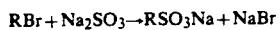

$$RBr + Na_2SO_3 \rightarrow RSO_3Na + NaBr$$

where R is as heretofore defined.

Long-chain sulphuric acid esters, for example sodium lauryl sulphate, and dioctylsulphosuccinate are readily available commercially.

The process is conducted in accordance with the following stages:

a) enriching the yeast with SAMe by adding methionine to cultures of *Saccharomyces cerevisiae, Torulopsis utilis, Candida utilis* etc., under the conditions described by Schlenk, Enzymologia, 29, 283 (1965);

CONCENTRATION OF L-METHIONINE IN THE MEDIUM

The concentrations of S-adenosylmethionine in the yeast cells from cultures without methionine supplement usually are less than 1 μmole per gram of moist cell centrifugate. By addition of L-methionine to the culture medium, a great increase in the intracellular level of S-adenosylmethionine is achieved (see FIG. 1). Quantities above 8 μmoles/ml, however, do not improve the yield. The efficiency of conversion of L-methionine into S-adenosylmethionine reaches a maximum at 3.0 μmoles of supplement per ml of culture medium. Below this level, methionine enters into reaction other than the formation of the sulfonium compound. Beyond the maximum of efficiency, the amino acid is no longer the limiting factor in this system. The yeast in this experiment (FIG. 1) was obtained from the National Yeast Corporation. An analogous experiment carried out earlier with dried yeast from Anehuser-Busch gave a maximum of conversion at a level of 2.0 μmoles of L-methionine per ml. A concentration of 11 μmoles of S-adenosylmethionine per g of yeast was acheived. The maximum level of the sulfonium compound was 24 μmoles/g with a supplement of 8.0 μmoles of L-methionine in the culture medium. Comparison of these data with the results listed in FIG. 1 show the similarity of the two yeasts.

For preparation of non-labeled S-adenosylmethionine, a concentration of 8 to 10 μmoles of L-methionine is recommended as supplement in the medium. As excess of the amino acid shows no harmful effects. For economy, a concentration of 2 to 3 μmoles is advisable when labeled L-methionine is used. Experiments with DL-methionine corresponding to those with L-methionine (FIG. 1) showed that the D-component is neither stimulating nor inhibitory. Some labeled varieties of methionine are available only in the DL-form. The concentration in the medium should be doubled in this case. In contrast to bakers' yeast (*Saccharomyces cerevisiae*), *Candida utilis* used both stereoisomers for the synthesis of S-adenosyl-DL-methionine.

The low rate of conversion of labeled methionine into S-adenosylmethionine might suggest a second use of the culture medium after replenishment with nutrients and another aliquot of yeast. In our experience, this is not possible because the spent medium contain unidentified inhibitors. Moreover, only a small fraction of the precursor methionine is left in the medium; most of it is assimilated by other reactions.

b) cell lysis followed by recovery of a SAMe-rich solution (ceel lysate): the lysis is effected by treating the enriched yeast firstly with a solution of water and ethyl acetate in a volume ratio of between 3:1 and 0.5:1, and preferably between 1.2:1 and 0.8:1, the quantity of water-ethyl acetate solution used is between 1/20 and ½, and preferably between ¼ and 1/5 of the moist cell weight, and the treatment is continued for a time of between 15 and 45 minutes, and preferably 30 minutes. Sulphuric acid of between 0.1N and 0.5N, and preferably 0.35N, is then added in a qualtity of between 1:1 and 0.2:1, and preferably between 0.5:1 and 0.6:1, with respect to the moist cell weight. The treatment is continued for a time of between 1 and 2 hours and preferably 1.5 hours, at ambient temperature. The cell lysis effected in this manner causes practically 100% of the SAMe present to pass into solution;

c) purification of the cell lysate; this is preferably effected by subjecting the lysate from stage b) to ultrafiltration, using membranes with a 10,000 nominal cut-off, which enable the protein residues and high-molecular weight polysaccharide residues to be removed, and which would otherwise fix on to the SAMe precipitate by adsorption;

d) precipitation of the SAMe salt: an aqueous solution is prepared by dissolving, for each mole of SAMe in the cell lysate to be precipitated, between 2.5 and 5 moles, and preferably about 3.5 moles of the required sulphonic acid sodium salt, or of the required sulphuric acid ester, or of dioctylsulphosuccinate, in the minimum quantity of distilled water, possibly heating in order to facilitate dissolving, and then cooling; said solution is acidified with 2 moles of sulphuric acid per mole of SAMe to be precipitated, and is added to the cell lysate as obtained from the preceding stages, to immediately form the insoluble SAMe salt, which precipitates in the proportion of 3 moles of acid per mole of SAMe. The reaction mixture is kept under agitation for 30 minutes;

e) filtration and drying: filtration can be effected by the normal apparatus and methods; it is preferably effected in a pressure filter or centrifuge; the product is carefully washed with distilled water and dried under vacuum at a temperature preferably of between 50° and 20° C., with a residual vacuum of less than 1 mm Hg.

By operating in accordance with the described process, the SAMe yield is between 80% and 95%, and the purity of the SAMe salts obtained is an average of 99%.

The SAMe salts according to the present invention are particularly suitable for use in oral pharmaceutical forms which contain them as active principle, either alone or coupled with pharmaceutically acceptable excipients and solid auxiliary agents.

The product can be presented in various pharmaceutical forms such as tablets, pills, capsules, sustained-release capsules, sustained-release tablets, gastroresistant tablets, sachets, syrups, extemporaneous syrups, sustained-release syrups and other forms normally used in pharmacy.

It is also possible to use the new SAMe salts in pharmaceutical forms which are absolutely new for SAMe, such as suppositories, creams, or ointments.

As stated heretofore, the main advantage of the new SAMe salts according to the present invention is their high absorption into the gastro-intestinal tract when compared with water-soluble SAMe salts known up to the present time.

The absorption was studied on 110 Sprague Dawley male rats of weight 210 g which had fasted since the previous evening.

The products are administered in solution or in a 2% gum arabic aqueous suspension.

For each product, 5 rats are operated under ether anesthesia to allow the substance under examination to be introduced into the proximal jejunum. The wall incision is closed by ligature, and the animals sutured.

The product is administered to a further 5 animals orally by means of a gastric probe.

A blood sample is withdrawn from the caudal vein at the commencement and at 10, 20, 40, 60, 90, 120, 180 and 240 minutes after administration, and the SAMe concentration is determined on the sample by the modified method of Baldessarini and Kopin (J. Neurochem. 13: 769, 1966).

The plasmatic concentration values less the initial values are plotted against time and the areas under the time curves to infinity calculated by the trapezium and curve extrapolation method.

The results obtained are given in Table 1, and show a considerably higher absorption for the SAMe salts according to the present invention than for other SAMe salts.

TABLE 1

Areas under the SAMe plasmatic concentration curves (AUC) for rats treated intestinally and orally with the listed products at a dosage corresponding to 100 mg of active principle per kg of body weight. The values represent the mean of 5 observations.

| Product | AUC (N moles · ml$^{-1}$ × min) | |
|---|---|---|
| | Oral administration | Intestinal administration |
| SAMe SO$_4$-PTS | 990 | 6700 |
| S1 | 870 | 4400 |
| S5 | 950 | 4900 |
| S6 | 980 | 6900 |
| S12 | 9700 | 25500 |
| S14 | 9800 | 26800 |
| S16 | 9600 | 25300 |
| S18 | 9400 | 24100 |
| SO12 | 8900 | 20800 |
| DSS | 8000 | 18500 |
| DBS | 7800 | 17000 | where:
SAMe SO$_4$-PTS = SAMe disulphate-p-toluenesulphonate
S1 = SAMe tri methanesulphonate
S5 = SAMe tri pentanesulphonate
S6 = SAMe tri hexanesulphonate
S12 = SAMe tri dodecanesulphonate
S14 = SAMe tri tetradecanesulphonate
S16 = SAMe tri hexadecanesulphonate
S18 = SAMe tri octadecanesulphonate
SO12 = SAMe tri laurylsulphonate
DSS = SAMe tri dioctylsulphosuccinate
DBS = SAMe tri dodecylbenzenesulphonate Illustrative but non-limiting examples of the process for preparing SAMe salts according to the present invention and of pharmaceutical formulations prepared with said salts are given hereinafter.

EXAMPLE 1

Preparation of Sulphonic Acid Sodium Salts of General Formula RSO3Na 80 liters of distilled water, 10 liters of 95% ethanol and 10 liters of n-butanol are added to 27.7 kg (100 moles) of 1-bromotetradecane. 13.9 kg (110 moles) of anhydrous sodium sulphite are added, and the mixture heated under reflux for 5 days.

On termination of the reaction, the mixture is diluted with 300 liters of distilled water, heated until complete dissolution has taken place, and the product allowed to crystallise overnight at 15° C.

The tetradecanesulphonic acid sodium salt obtained in this manner is filtered off, washed with 50 l of distilled water and then with 50 l of acetone in successive portions.

The product is suspended in 50 l of acetone, heated to 50° C. to extract the myristic alcohol which had formed during the reaction, left to cool and filtered off. It is washed with acetone and dried under vacuum.

24 kg of tetradecanesulphonic acid sodium salt are obtained (molar yield about 80%) as a crystalline white powder soluble in water to 1% at 40° C. to give a clear colourless solution.

| Elementary analysis: C$_{14}$H$_{29}$O$_3$SNa | | | |
|---|---|---|---|
| | % C | % H | % S |
| Calculated | 56.0 | 9.7 | 10.7 |
| Found | 56.0 | 9.6 | 10.6 |

Using 24.5 kg of 1-bromododecane and operating in a manner exactly similar to that described, 21.7 kg of dodecanesulphonic acid sodium salt are obtained.

Using 30.5 kg of 1-bromohexadecane, 26.3 kg of hexadecanesulphonic acid sodium salt are obtained.

Finally, using 33.3 kg of 1-bromooctadecane, 28.5 kg of octadecanesulphonic acid sodium salt are obtained.

EXAMPLE 2

Preparation of SAMe tri hexadecanesulphonate (S16)

220 liters of ethyl acetate and 220 liters of water are added at ambient temperature to 1800 kg of yeast enriched with SAMe (6.88 g/kg) in accordance with Schlenk [Enzymologia 29, 283(1965)].

After energetic agitation for 30 minutes, 1000 liters of 0.35N sulphuric acid are added, and agitation continued for a further 1½ hours.

It is filtered through a rotary filter which is washed with water to obtain 2800 liters of a solution containing 4.40 g/l of SAMe, equivalent to 99.5% of that present in the starting material.

The SAMe solution obtained in this manner (pH 2.5) is fed to an ultrafiltration plant using tubular membranes of 10,000 cut-off.

The permeate leaving the membranes is collected in a suitable vessel, whereas the concentrate is continuously recycled to a final volume of 200 liters. At this point, distilled water is added and recyling is continued until the SAMe is completely extracted. 3500 liters of ultrafiltered lysate are obtained containing 12.2 kg of SAMe ion.

35 kg of sodium hexadecanesulphonate are dissolved separately in 2500 l of deionised water at 50° C., and 6 kg of concentrated sulphuric acid are added.

The solution thus obtained is added to the cell lysate. A precipitate immediately forms. The mixture is cooled to 20° C. and left under agitation for 30 minutes. The precipitate is filtered off through a pressure filter and washed with 300 liters of distilled water.

It is then placed in a vacuum dryer at 40° C. and 0.5 mm Hg of residual pressure until the residual moisture content of the product is less than 1%.

37 kg of white powder are obtained, which on analysis shows the following composition:
SAMe: 30.2%
Hexadecanesulphonic acid: 69.6%
H$_2$O: 0.2%
corresponding to the salt SAMe.3 hexadecanesulphonate.

The product is in the form of a white powder insoluble in water and slightly soluble in methanol, ethanol and acetone. It is soluble in 2:1 methanol-chloroform mixture to 5% at 25° C. with the formation of a colourless solution.

Thin layer chromatography in accordance with Anal. Biochem. 4, 16–28 (1971) shows that the product is free from any impurity.

| Elementary analysis: C$_{15}$H$_{22}$N$_6$O$_5$S.3C$_{16}$H$_{34}$O$_3$S | | | |
|---|---|---|---|
| | % N | % C | % H |
| Calculated | 6.4 | 57.4 | 9.4 |
| Found | 6.4 | 57.3 | 9.4 |

The ultraviolet spectrum for the product (3 mg in 100 ml 1:1 water-methanol) shows an absorption maximum at 259 nm with E$_{1\%}$ = 106.7.

EXAMPLE 3

Preparation of SAMe tri octadecanesulphonate (S18)

The procedure of Example 2 is followed to obtain 3500 liters of ultrafiltered lysate which contain 12.2 kg of SAMe ion.

38 kg of sodium octadecanesulphonate are dissolved in 3400 liters of deionised water at 50° C., and 6 kg of concentrated sulphuric acid are added. The procedure of Example 2 is followed to obtain 40 kg of white powder, which on analysis shows the following composition:

SAMe: 28.5%
Octadecanesulphonic acid: 71.3%
$H_2O$: 0.2% corresponding to the salt SAMe.3 octadecanesulphonate.

The product is in the form of a white powder insoluble in water and in methanol, ethanol and acetone.

It is soluble in 1:1 methanol-chloroform mixture to 5% at 20° C. with the formation of a colourless solution. Thin layer chromatography in accordance with Anal. Biochem. 4, 16–28 (1971) shows that the product is free from any impurity.

| Elementary analysis: $C_{15}H_{22}N_6O_5S.3C_{18}H_{38}O_3S$ | | | |
|---|---|---|---|
|  | % N | % C | % H |
| Calculated | 6.0 | 59.1 | 9.7 |
| Found | 6.1 | 59.2 | 9.7 |

The ultraviolet spectrum for the product (3 mg in 100 ml of a mixture of 10% chloroform, 60% methanol, 30% water) shows an absorption maximum at 259 nm with $E_{1\%} = 100.3$.

EXAMPLE 4

Preparation of SAMe tri tetradecanesulphonate (S14)

The procedure of Example 2 is followed to obtain 3500 liters of ultrafiltered lysate which contain 12.2 kg of SAMe ion.

32 kg of sodium tetradecanesulphonate are dissolved in 2000 liters of deionised water at 50° C., and 6 kg of concentrated sulphuric acid are added.

The procedure of Example 2 is followed to obtain 34 kg of white powder which on analysis shows the following composition:

SAMe: 32.3%
Tetradecanesulphonic acid: 67.5%
$H_2O$: 0.2% corresponding to the salt SAMe.3 tetradecanesulphonate.

The product is in the form of a white powder insoluble in water and soluble in methanol or ethanol to 5% with the formation of a colourless solution.

Thin layer chromatography in accordance with Anal. Biochem. 4, 16–28 (1971) shows that the product is free from any impurity.

| Elementary analysis: $C_{15}H_{22}N_6O_5S.3C_{14}H_{30}O_3S$ | | | |
|---|---|---|---|
|  | % N | % C | % H |
| Calculated | 6.8 | 55.6 | 9.1 |
| Found | 6.8 | 55.5 | 9.2 |

The ultraviolet spectrum for the product (3 mg in 100 ml of 1:1 water-methanol) shows an absorption maximum at 259 nm with $E_{1\%} = 114$.

EXAMPLE 5

Preparation of SAMe tri dodecanesulphonate (S12)

The procedure of Example 2 is followed to obtain 3500 liters of ultrafiltered lysate containing 12.2 kg of SAMe ion.

The lysate is adjusted to pH 6 by adding 2N NaOH. A column is prepared containing 200 liters of Amberlite CG50 resin in $H^+$ form carefully washed with distilled water.

The lysate is passed through the resin column at a rate of 600 l/h kept constant during the entire procedure. 200 liters of distilled water, 400 liters of 0.1M acetic acid and 200 liters of distilled water are then passed through successively. The SAMe is eluted with 500 liters of 0.25N sulphuric acid.

The 500 liters of eluate obtained in this manner contain 11.5 kg of SAMe ion.

23.5 kg of sodium dodecanesulphonate are dissolved in 1000 liters of deionised water at 40° C., and 4.5 kg of concentrated sulphuric acid are added.

The solution thus obtained is added to the eluate containing the SAMe. A precipitate immediately forms.

The mixture is cooled to 20° C. and left under agitation for 30 minutes.

The precipitate is filtered off in a pressure filter and washed with 300 liters of distilled water. It is dried in a vacuum dryer at 40° C. under 0.5 mm Hg of residual pressure until the residual moisture content of the product is less than 1%.

30.3 kg of white powder are obtained, which on analysis shows the following composition:

SAMe: 34.6%
Dodecanesulphonic acid: 65.2%
$H_2O$: 0.2% corresponding to the salt SAMe.3 dodecanesulphonate.

The product is in the form of a white powder insoluble in water and soluble in methanol, ethanol and isopropanol to 5% with the formation of a colourless solution.

Thin layer chromatography in accordance with Anal. Biochem. 4, 16–28 (1971) shows that the product is free from any impurity.

| Elementary analysis: $C_{15}H_{22}N_6O_5S.3C_{12}H_{26}O_3S$ | | | |
|---|---|---|---|
|  | % N | % C | % H |
| Calculated | 7.3 | 53.3 | 8.7 |
| Found | 7.4 | 53.3 | 8.8 |

The ultraviolet spectrum for the product (3 mg in 100 ml of 1:1 water-methanol) shows an absorption maximum at 259 nm with $E_{1\%} = 122.3$.

EXAMPLE 6

Preparation of SAMe tri laurylsulphate (SO12)

The procedure of Example 5 is followed to obtain 500 liters of eluate containing 11.5 kg of SAMe ion.

27.7 kg of commercially available 90% sodium lauryl sulphate U.S.P. are dissolved in 500 liters of distilled water, and 4.5 kg of concentrated sulphuric acid are added.

The procedure of Example 5 is continued to obtain 30.6 kg of white powder which on analysis shows the following composition:
SAMe: 33.3%
Laurylsulphuric acid: 66.5%
H₂O: 0.2%
corresponding to the salt SAMe.3 laurylsulphate.

The product is in the form of a white powder insoluble in water and soluble in methanol and ethanol to 5% with the formation of a colourless solution.

Thin layer chromatography in accordance with Anal. Biochem. 4, 16–28 (1971) shows that the product is free from any impurity.

| Elementary analysis: $C_{15}H_{22}N_6O_5S.3C_{12}H_{26}O_4S$ | | | |
|---|---|---|---|
| | % N | % C | % H |
| Calculated | 7.0 | 51.2 | 8.4 |
| Found | 7.0 | 51.3 | 8.3 |

The ultraviolet spectrum for the product (3 mg in 100 ml of 1:1 water-methanol) shows an absorption maximum at 259 nm with $E_{1\%} = 117.4$.

EXAMPLE 7

Preparation of SAMe tri dodecylbenzenesulphonate (SB12)

The procedure of Example 5 is followed to obtain 500 liters of eluate containing 11.5 kg of SAMe ion.

35.5 kg of commercial 85% sodium dodecylbenzenesulphonate are dissolved in 600 liters of deionised water, and 4.5 kg of concentrated sulphuric acid are added.

(It should be noted that the term "sodium dodecylbenzenesulphonate" is the commercial name for a mixture of sodium alkyl-benzenesulphonates having the following average composition:

$C_{10} = 5\%$, $C_{11} = 45$–$50\%$, $C_{12} = 35\%$, $C_{13} = 10$–$15\%$, $C_{14} < 0.05\%$.

corresponding to an empirical formula of $C_{18}H_{29}O_3SNa$).

The procedure of Example 5 is followed to obtain 35 kg of slightly yellow powder which on analysis shows the following composition:
SAMe: 30%
Dodecylbenzenesulphonic acid: 69.8%
H₂O: 0.2%
corresponding to the salt SAMe.3 dodecylbenzenesulphonate.

The product is in the form of a yellow powder insoluble in water and soluble in methanol and ethanol to 5% to form a clear solution.

Thin layer chromatography in accordance with Anal. Biochem. 4, 16–28 (1971) shows that the product is free from any impurity.

| Elementary analysis: $C_{15}H_{22}N_6O_5S.3C_{18}H_{30}O_3S$ | | | |
|---|---|---|---|
| | % N | % C | % H |
| Calculated | 6.1 | 60.2 | 8.1 |
| Found | 6.2 | 60.1 | 8.1 |

The ultraviolet spectrum for the product (3 mg in 100 ml of 1:1 water-methanol) shows an absorption maximum at 259 nm with $E_{1\%} = 109$.

EXAMPLE 8

Preparation of SAMe tri "dioctylsulphosuccinate"

The procedure of Example 5 is followed to obtain 500 liters of eluate containing 11.5 kg of SAMe ion.

38.5 kg of commercial dioctylsulphosuccinate sodium salt are dissolved in 2000 liters of deionised water at 40° C., and 4.5 kg of concentrated sulphuric acid are added.

The procedure of Example 5 is continued to obtain 43.5 kg of white powder which on analysis shows the following composition:
SAMe: 24%
Dioctylsulphosuccinic acid: 75.8%
H₂O: 0.2%
corresponding to the salt SAMe.3 dioctylsulphosuccinate.

The product is in the form of a white powder insoluble in water and soluble in methanol and ethanol to 5% with the formation of a colourless clear solution.

Thin layer chromatography in accordance with Anal. Biochem. 4, 16–28 (1971) shows that the product is free from any impurity.

| Elementary analysis: $C_{15}H_{22}N_6O_5S.3C_{20}H_{38}O_7S$ | | | |
|---|---|---|---|
| | % N | % C | % H |
| Calculated | 5.0 | 54.1 | 8.2 |
| Found | 5.1 | 54.1 | 8.3 |

The ultraviolet spectrum for the product (3 mg in 100 ml of 1:1 water-methanol) shows an absorption maximum at 259 nm with $E_{1\%} = 84.4$.

EXAMPLE 9

Preparation of SAMe tri undecanesulphonate

The procedure of Example 5 is followed to obtain 500 liters of eluate containing 11.5 kg of SAMe ion.

22.5 kg of sodium undecanesulphonate are dissolved in 500 liters of water at 40° C., and 4.5 kg of concentrated sulphuric acid are added.

The procedure of Example 5 is followed to obtain 29 kg of white powder which on analysis shows the following composition:
SAMe: 36%
Undecanesulphonic acid: 63.8%
H₂O: 0.2%
corresponding to the salt SAMe.3 undecanesulphonate.

The product is in the form of a white powder insoluble in water and soluble in methanol and ethanol to 10% with the formation of a colourless clear solution.

Thin layer chromatography in accordance with Anal. Biochem. 4, 16–28 (1971) shows that the product is free from any impurity.

| Elementary analysis: $C_{15}H_{22}N_6O_5S.3C_{11}H_{24}O_3S$ | | | |
|---|---|---|---|
| | % N | % C | % H |
| Calculated | 7.6 | 52.1 | 8.5 |
| Found | 7.6 | 52.2 | 8.6 |

The ultraviolet spectrum for the product (3 mg in 100 ml of 1:1 water-methanol) shows an absorption maximum at 259 nm with $E_{1\%} = 127$.

EXAMPLE 10

Preparation of SAMe tri decanesulphonate

The procedure of Example 5 is followed to obtain 500 liters of eluate containing 11.5 kg of SAMe ion.

21.5 kg of sodium decanesulphonate are dissolved in 400 liters of deionised water at 40° C., and 4.5 kg of concentrated sulphuric acid are added. The procedure of Example 5 is continued to obtain 26.6 kg of white powder which on analysis shows the following composition:

SAMe: 37.5%
Decanesulphonic acid: 62.3%
$H_2O$: 0.2% corresponding to the salt SAMe.3 decanesulphonate.

The product is in the form of a white powder insoluble in water and soluble in methanol and ethanol to 10% with the formation of a clear colourless solution.

Thin layer chromatography in accordance with Anal. Biochem. 4, 16-28 (1971), shows that the product is free from any impurity.

| Elementary analysis: $C_{15}H_{22}N_6O_5S.3C_{10}H_{22}O_3S$ | | | |
|---|---|---|---|
| | % N | % C | % H |
| Calculated | 7.9 | 50.8 | 8.3 |
| Found | 7.8 | 50.7 | 8.2 |

The ultraviolet spectrum for the product (3 mg in 100 ml of 1:1 water-methanol) shows an absorption maximum at 259 nm with $E_{1\%}=132$.

EXAMPLE 11

Preparation of Gastrosoluble Tablets

A 100 mg tablet contains:

| a) SAMe S16 | 330 mg |
|---|---|
| equivalent to SAMe ion | 100 mg |
| Cross-linked carboxymethyl cellulose sodium salt | 50 mg |
| Microcrystalline cellulose to make up to | 500 mg |
| b) SAMe S14 | 309 mg |
| equivalent to SAMe ion | 100 mg |
| Cross-linked polyvinylpyrrolidone | 100 mg |
| Sodium chloride | 100 mg |
| Microcrystalline cellulose to make up to | 600 mg |
| c) SAMe S12 | 288 mg |
| equivalent to SAMe ion | 100 mg |
| Sodium bicarbonate | 200 mg |
| Citric acid | 100 mg |

EXAMPLE 12

Preparation of Gastroresistant Tablets

A 100 mg tablet contains:

| a) SAMe S16 | 330 mg |
|---|---|
| equivalent to SAMe ion | 100 mg |
| Cross-linked carboxymethylcellulose sodium salt | 50 mg |
| Microcrystalline cellulose to make up to | 500 mg |
| Cellulose acetophthalate | 20 mg |
| Diethylphthalate | 6.4 mg |
| Silicone resin | 3.6 mg |
| b) SAMe S14 | 309 mg |
| equivalent to SAMe ion | 100 mg |
| Cross-linked polyvinylpyrrolidone | 100 mg |
| Sodium chloride | 100 mg |
| Microcrystalline cellulose to make up to | 600 mg |
| Cellulose acetophthalate | 20 mg |
| Diethylphthalate | 6.4 mg |
| Silicone resin | 3.6 mg |
| c) SAMe S12 | 288 mg |
| equivalent to SAMe ion | 100 mg |
| Sodium bicarbonate | 200 mg |
| Citric acid | 100 mg |
| Cellulose acetophthalate | 20 mg |
| Diethylphthalate | 6.4 mg |
| Silicone resin | 3.6 mg |

EXAMPLE 13

Preparation of Capsules

A 100 mg capsule contains:

| a) SAMe S18 | 351 mg |
|---|---|
| equivalent to SAMe ion | 100 mg |
| Lactose | 100 mg |
| Magnesium stearate | 12 mg |
| b) SAMe SO12 | 300 mg |
| equivalent to SAMe ion | 100 mg |
| Mannitol | 100 mg |
| Lactose | 50 mg |
| Magnesium stearate | 12 mg |

EXAMPLE 14

Preparation of Capsules with Chronoids

A 100 mg capsule with chronoids contains:

| a) SAMe S16 | 330 mg |
|---|---|
| equivalent to SAMe ion | 100 mg |
| Sugar chronoids | 200 mg |
| b) SAMe S14 | 309 mg |
| equivalent to SAMe ion | 100 mg |
| Sugar chronoids | 200 mg |

EXAMPLE 15

Preparation of Suppositories

A 100 mg suppository contains:

| a) SAMe S14 | 309 mg |
|---|---|
| equivalent to SAMe ion | 100 mg |
| Suppository mass to make up to | 2.5 g |
| b) SAMe S16 | 330 mg |
| equivalent to SAMe ion | 100 mg |
| Suppository mass to make up to | 2.5 g |
| c) SAMe S18 | 351 mg |
| equivalent to SAMe ion | 100 mg |
| Suppository mass to make up to | 2.5 g |

I claim:

1. A process for producing stable sulpho-adenosyl-L-methionine (SAMe) salts particularly suitable for oral pharmaceutical use, corresponding to the general formula:

SAMe.nR(O)$_m$(SO$_3$H)p  (I)

where m can be zero or 1; n is 1.5 when p is 2, and is 3 when p is 1; R is chosen from the group consisting of alkyl, phenylalkyl and carboxyalkyl, in which the linear or branched alkyl chain contains from 8 to 18 carbon atoms, and in particular for producing SAMe salts of sulphonic acids, or of sulphuric acid esters, or of dioctylsulphosuccinic acid, comprising:

a) enriching a culture of a starting yeast selected form the group consisting of Saccharomyces cerevisiae, and *Candida utilis* with SAMe by adding methionine to the culture under SAMe enriching conditions;

b) lysing the cells to produce a cell lysate in aqueous solution rich in SAMe and recovering the cell lysate by filtering the aqueous liquid;

c) purifying the cell lysate by ultrafiltration;

d) precipitating the SAMe with one of said acids or esters;

e) separating the precipitated product, washing it and drying it under vacuum.

2. A process for producing stable SAMe salts as claimed in claim 1, in which the starting culture of yeast is enriched with SAMe by adding methionine.

3. A process for producing stable SAMe salts as claimed in claim 1, in which the cell lysis is effected by treating the enriched yeast firstly with water and ethyl acetate and then with a sulphuric acid solution of between 0.1N and 0.5N.

4. A process for producing stable SAMe salts as claimed in claim 1, in which the cell lysate is purified by ultrafiltration, using membranes with a nominal cut-off of 10,000.

5. A process for producing stable SAMe salts as claimed in claim 1, in which the stable SAMe salt is precipitated by treating the cell lysate with said sulphonic acids or with said sulphuric acid esters or with said dioctylsulphosuccinic acid such that the molar ratio of said precipitants to SAMe is between 5:1 and 2.5:1.

6. A process for producing stable SAMe salts as claimed in claim 1, in which the precipitated product is separated by means of a pressure filter or a centrifuge, is washed with distilled water and is dried under vacuum at a temperature between 50° and 20° C. under a residual pressure of less than 1 mm Hg.

* * * * *